United States Patent [19]

Arena et al.

[11] Patent Number: 5,621,000
[45] Date of Patent: Apr. 15, 1997

[54] NITRIC ESTERS HAVING A PHARMACOLOGICAL ACTIVITY AND PROCESS FOR THEIR PREPARATION

[75] Inventors: Barbara Arena; Piero Del Soldato, both of Monza, Italy

[73] Assignee: Nicox S.A., Paris, France

[21] Appl. No.: 446,624

[22] PCT Filed: Nov. 15, 1993

[86] PCT No.: PCT/EP93/03193

§ 371 Date: May 26, 1995

§ 102(e) Date: May 26, 1995

[87] PCT Pub. No.: WO94/12463

PCT Pub. Date: Jun. 9, 1994

[30] Foreign Application Priority Data

Nov. 26, 1992 [IT] Italy .................................. MI92A2699

[51] Int. Cl.$^6$ .................... A61K 31/40; C07D 209/88
[52] U.S. Cl. .................... 514/411; 514/423; 514/448; 514/509; 548/432; 548/444; 548/472; 548/532; 549/72; 558/482
[58] Field of Search ..................... 548/444, 432, 548/472, 532; 549/72; 558/482; 514/411, 423, 448, 509

[56] References Cited

U.S. PATENT DOCUMENTS

| | | |
|---|---|---|
| 4,585,877 | 4/1986 | Demerson et al. . |
| 4,780,560 | 10/1988 | Kumonaka et al. .................... 558/482 |
| 4,988,728 | 1/1991 | Gerson et al. . |
| 5,366,992 | 11/1994 | Sala et al. ................................ 514/409 |

FOREIGN PATENT DOCUMENTS

| | | |
|---|---|---|
| 0359335 | 9/1988 | European Pat. Off. . |
| 0300400 | 1/1989 | European Pat. Off. . |
| 2612185 | 3/1988 | France . |
| WO9201668 | 2/1992 | WIPO . |

*Primary Examiner*—Jacqueline Haley
*Attorney, Agent, or Firm*—Hale and Dorr LLP

[57] ABSTRACT

Nitric esters with pharmacological activity having general formula (I), their pharmaceutical utilisation and process for their preparation.

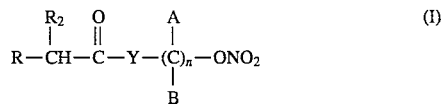

17 Claims, No Drawings

NITRIC ESTERS HAVING A PHARMACOLOGICAL ACTIVITY AND PROCESS FOR THEIR PREPARATION

This application is a National Stage Application of PCT/EP93/03193 filed Nov. 15, 1993 and published as WO 94/12463 on Jun. 9, 1994.

Object of the present invention are nitric esters with an anti-inflammatory and/or anti-platelet aggregation activity, their pharmaceutical utilization and the process for their preparation.

PRIOR ART

Some derivatives of propionic acid, such as for instance 2-(-3-benzoylphenyl)propionic acid, commonly known as ketoprofen, have been used for a long time as pharmaceutical preparations for their anti-inflammatory activity and are sold on the different international markets since many years. The process for the preparation of 2-(3-benzoylphenyl)propionic acid has been described in the South African patent no. 68 00,524, corresponding to the US Pat. No. 3,641,127; in the French patent no. M6444 and also in C.A. 75,5528m (1971); G. A. PINNA et al., FARMACO Ed. Sci. 35,684 (1980); while the pharmacokinetics in humans is described in T. ISHIZAKI et al., Eur. J. Clin. Pharmacol. 18,407 (1980). The use of derivatives of propionic acid, such as, for instance, keptofren, as well as the use of other products which are utilized as anti-inflammatory agents, involves, as known, severe adverse reactions, for instance in the gastrointestinal apparatus, as well as possible damages to the liver and the kidneys.

There is much experimental evidence [S. MONCADA, R. M. J. PALMER, E. A. HIGGS, Pharmacological Reviews, 43(2), 109 (1991); T. H. LUSHER, C. M. BOUGLANGER, Y. DOHI, Z. YANG, Hypertension, 19,117 (1992)], on whose basis the integrity of vasal endothelium is thought to be a basic barrier against the onset of pathological processes in several organs and apparatuses.

Such protection barrier, and therefore the integrity of the vasal endothelium, is ensured physiologically by the presence of nitric oxide and prostacyclin. The treatment with non steroid drugs having an anti-inflammatory activity, such as, for instance, 2-(3-benzoylphenyl)propionic acid or ketoprofen, causes the inhibition of cyclo-oxygenase, an enzyme which syntesizes the precursor of prostacyclin.

As a consequence, having so inhibited the production of prostacyclin, the reserve of same in the tissues is markedly depauperated, and therefore the integrity of vasal endothelium is compromised.

As said, because of this endothelial damage due to the reduction of prostacyclin, diffuse pathological process break out which affect the gastrointestinal apparatus, liver and kidneys.

OBJECTS OF THE INVENTION

Object of the present invention is that to provide a group of products which, while ensuring the maintenance of the pharmacological activity characteristic of the known anti-inflammatory agents, are capable of eliminating the adverse reactions caused by the treatment with said agents.

Another object of the present invention is the realization of a process for the preparation of a group of products having an anti-inflammatory activity while being exempt from the adverse reactions which are typical of anti-inflammatory agents.

DESCRIPTION OF THE INVENTION

These and still other objects and associated advantages which will appear from the following description, are obtained with nitric esters having the following general formula:

$$R-\underset{\underset{R_2}{|}}{C}H-\underset{\underset{}{||}}{\overset{O}{C}}-Y-\underset{\underset{B}{|}}{(C)_n}-ONO_2 \quad (I)$$

where:

A and B are chosen among hydrogen, linear or branched, substituted or non substituted alkyl chains, R is chosen among

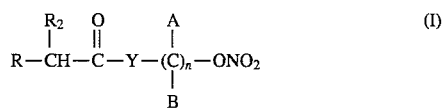 (II)

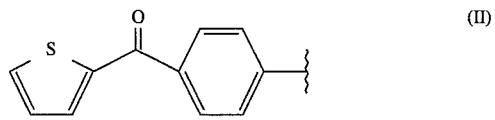 (III)

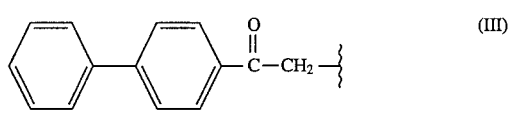 (IV)

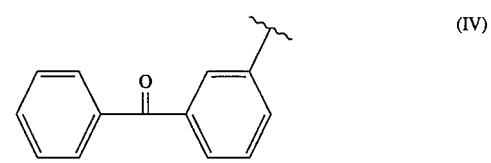 (VI)

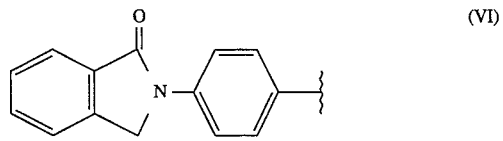 (VII)

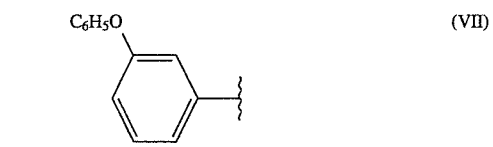 (VIII)

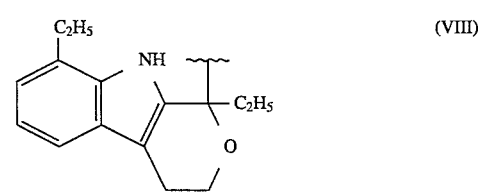 (IX)

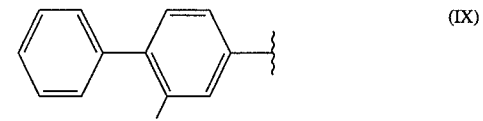

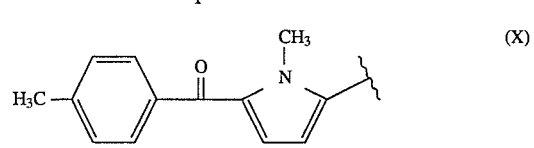 (X)

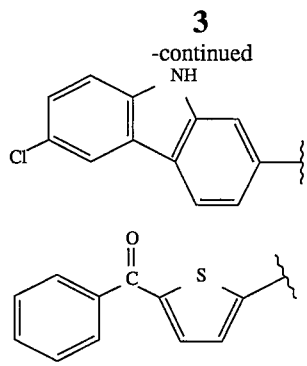

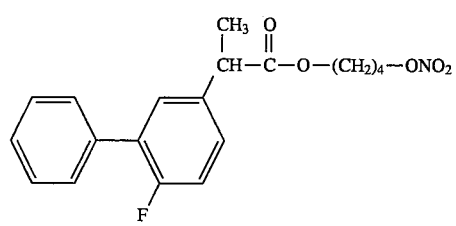

$R_2$ is chosen among hydrogen, methyl, ethyl, alkyl chains linear or branched by 3 to 12 carbon atoms, substituted or non substituted, Y is chosen among oxygen, NH, $NR_1$, where $R_1$ is a linear or branched alkyl group and n is comprised between 1 and 10.

In fact, it has been observed that the introduction of a group such as a terminal nitric ester in the general formula derivatives (I) allows to maintain the pharmacological activity characteristic of non steroid anti-inflammatory agents, while eliminating the adverse reactions caused by the treatment with such agents. Besides, it has been observed that derivatives (I) are useful also in the treatment of various morbid conditions, such as, for instance, rheumatic diseases in general, disorders of immunologic nature, and can also assuage light-middle severity painful conditions of any kind.

More still, the derivatives (I) subject matter of this invention, are useful in the treatment of diseases of the cardiovascular apparatus, and in particular in the treatment of miocardial and brain ischemiae as well as in artery thrombosis as anti-platelet aggregation agents.

Always according to this invention, a nitric ester of general formula (I) proved particularly advantageous, where:

hydrogen is chosen as A and B, methyl is chosen as $R_2$, and as R is chosen

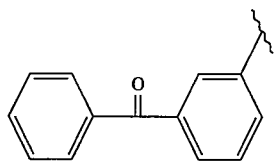

oxygen is chosen as y and n is equal to four, according to the following formula:

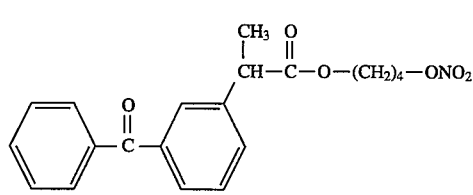

Also particularly advantageous according to this invention is the nitric ester of a general formula (I) where:

hydrogen is chosen as A and B, as R is chosen

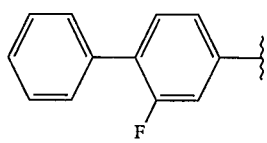

methyl is chosen as $R_2$ oxygen is chosen as Y and n is equal to four, according to the following formula:

Still more, always according to the present invention, particularly advantageous are the nitric esters of general formula derivatives (I) where: hydrogen is chosen as A and B, as R are chosen

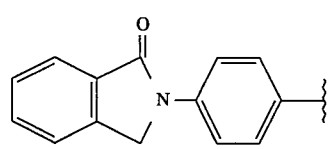

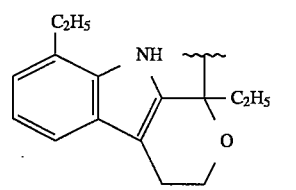

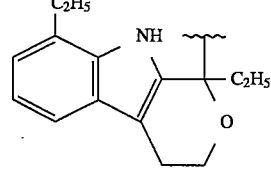

methyl, ethyl and hydrogen are chosen as $R_2$, oxygen is chosen as y and n is equal to four, according to the following formulae:

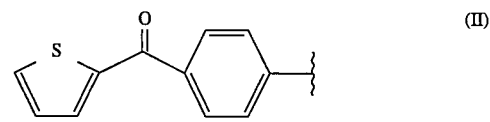

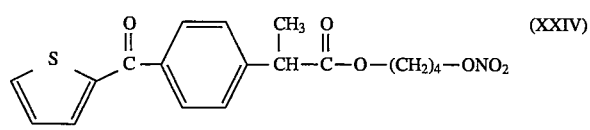

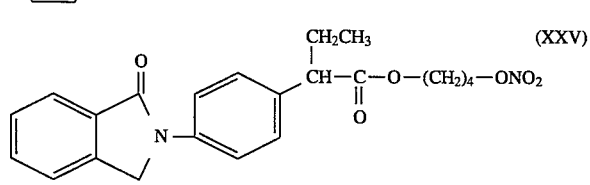

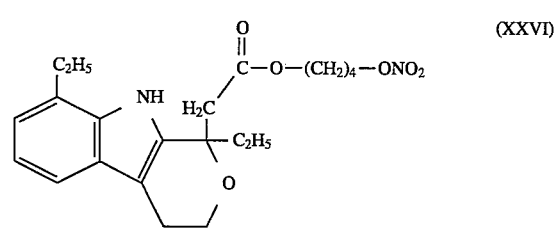

For the preparation of general formula nitric esters (I), subject matter of the present invention, particularly advantageous proved to be a first process which, according to the invention, comprises the following steps:

Preparation of the sodium salt of the products having the following general formula:

where $R_2$ is chosen among hydrogen, methyl, ethyl, alkyl chains linear or branched by 3 to 12 carbon atoms, substituted or non substituted, R is chosen among: (II), (III), (IV), (VI), (VII), (VIII), (IX), (X), (XXI), (XXXV) or preparation of derivatives (XIV) functionalized to the carboxyl group, such as acilic chlorides, anhydrides or the like;

Reaction between the sodium salt of said derivatives (XIV) or between said derivatives (XIV) functionalized to the carboxylic group, with a composition having the following general formula:

(XV)

where:

$R_4$ is chosen among chlorine, bromine, $NHR_6$ with $R_6$ chosen among hydrogen, lineal or branched alkyl chain, A and B are chosen among hydrogen, linear or branched, substituted or non substituted alkyl chains, $R_3$ is chosen among chlorine, bromine, and iodine, and n is comprised between 1 and 10, obtaining in this way the relative monomeric esters or the relative amides;

Reaction of said monomeric esters or said amides with a nitrating agent such as $AgNO_3$ or the like, obtaining in this way nitric esters of derivatives (I).

Also a second process proved to be particularly advantageous which, always according to the present invention, comprises the following steps:

Preparation of the sodium salt of derivatives having the following general formula:

(XIV)

where R is chosen among: (II), (III), (IV), (VI), (VII), (VIII), (IX), (X), (XXI), (XXXV)

$R_2$ is chosen among hydrogen, methyl, ethyl, alkyl chains linear or branched by 3 to 12 carbon atoms, substituted or non substituted, or, alternatively, preparation of derivatives (XIV) functionalized to the carboxylic group, such as acidic chlorides, anhydrides or the like;

Reaction between the sodium salt of said derivatives (XIV) or between said derivatives (XIV) functionalized to the carboxylic group, with a composition having the following general formula:

(XVI)

where:

$R_4$ is chosen among chlorine, bromine, $NHR_6$ with $R_6$ equal to hydrogen, or linear or branched alkyl chain, A and B are chosen among hydrogen, linear or branched, substituted or non substituted alkyl chains, and n is comprised between 1 and 10, obtaining in this way the relative monomeric esters or amides;

Reaction of said monomeric esters or said amides with an halogenating composition such as $PBr_3$ or the like, obtaining in this way said monomeric esters or said amides characterized by the presence of a terminal halogen group;

Reaction of said monomeric esters or said amides characterized by the presence of a terminal halogen group, with a nitrating agent such as $AgNO_3$ or the like, obtaining in this way nitric esters of derivatives (I).

The solvents utilized in the processes subject matter of this invention are preferably chosen among chloroform, methylene chloride, acetonitrile, dimethylformamide, tetrahydrofuran, 1,4-dioxane and the like.

The processes for the preparation of derivatives (I) subject matter of this invention, consist of a limited number of steps, allowing to obtain the products which derive from said processes in a short time and with satisfactory yields even on the industrial plane.

According to the processes subject matter of this invention, the preparation of a nitric ester having the following formula:

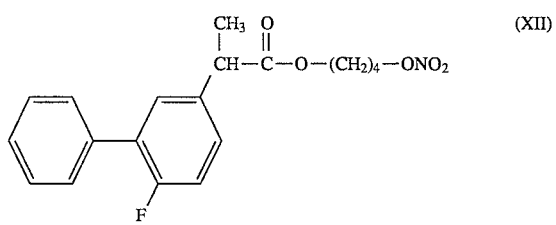

(XII)

proved to be particularly advantageous, which is prepared as described in the following example, given as a mere indication without limiting the protection scope of this invention.

EXAMPLE 1 a) 2 g of 2-fluoro-alpha-methyl-4-diphenylacetic acid were added to a solution constituted by 10 ml of methyl alcohol and 0.23 g of Na. The reaction mix was stirred for 5 minutes, then the solvent was evaporated under reduced pressure, obtaining the sodium salt of 2-fluoro-alpha-methyl-4-diphenylacetic acid.

b) The sodium salt of 2-fluoro-alpha-methyl-4-diphenilacetic acid obtained in this way was suspended in 20 ml of dimethylformamide and 3 ml of 1,4-dibromo-butane were added by dripping to this suspension. The reaction mix was stirred for 22 hours at room temperature, then the NaBr which had formed was filtered and the solvent was evaporated under reduced pressure. The residue so obtained was treated with methylene chloride and, after elimination by filtration of the insoluble residue, the methylene chloride was evaporated under reduced pressure, obtaining 3 g of a dry residue which was purified by silica gel chromatography, utilizing an eluent mix constituted by hexane/methylene chloride 1/1 (V/V). The head fractions were collected, the solvent was evaporated under reduced pressure and 1.86 g of 2-fluoro-alpha-methyl-4-diphenylacetate of 4-bromobutyl (XXII) were obtained.

IR $(cm^{-1})$: C=0,1470

$^1$-H-NMR (300 MHz) $(CDCl_3)$ : 1.51 ppm (d, 3H); 1.56 ppm (m,4H); 3,35 ppm (t,2H); 3.61 ppm (q,1H); 4.1 ppm (t, 2H); 7.05 ppm (m, 1H); 7.17 ppm (s, 1H); 7.3–7.55 (m, aromatics).

c) 1.2 g of $AgNO_3$ dissolved in 8.3 ml of acetonitrile were added to 1.86 g of (XXII), obtained as described under b) dissolved in 7.5 ml of acetonitrile. The reaction mix was stirred for 48 hours at room temperature and then filtered. The solvent was evaporated from the resulting solution under reduced pressure, obtaining a residue which was treated with methylene chroride. The mix obtained in this way was filtered again and the organic phase was purified by silica gel pressure chromatography, utilizing an eluent mix constituted by diethylether/hexane 3/7 (V/V). The fractions containing the products were collected, the solvent was evaporated under reduced pressure and 1.2 g of nitric ester of 2-fluoro-alpha-methyl-4-diphenyl acetate of 4-hydroxybutyl (XII) were obtained.

IR(cm$^{-1}$): C=0,1737; ONO$_2$, 1623, 1274.

$^1$H-NMR (300 MHz) (CDCl$_3$): 1.53 ppm (d,3H); 1.72 ppm (m,4H); 3.74 ppm (q,1H); 4.13 ppm (t,2H); 4.4 ppm (t,2H); 7.13 ppm (t,2H, aromatics); 7.32–7.42 ppm (m,4H, aromatics); 7.53 ppm (m,2H, aromatics).

Mass spectrometry (i.e.): (M$^+$)361; (M+1-NO$_2$)316; 243; 199.

Always according to the processes subject matter of the present invention, also the preparation of a nitric ester having the following formula:

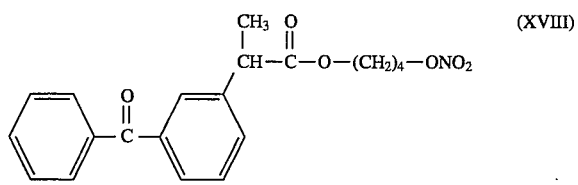
(XVIII)

proved particularly advantageous, which is prepared as described in the example shown hereunder, given as a mere indication without limiting the protection scope of this invention.

EXAMPLE 2 a) 10 g of 2-(3-benzoilphenyl)propionic acid were added to a solution constituted by 80 ml of methyl alcohol and 1.19 g of Na. The reaction mix was stirred for 15 minutes, then the solvent was evaporated under reduced pressure, obtaining a residue constituted by the sodium salt of 2-(3-benzoilphenyl)propionic acid.

b) 100 ml of dimethylformamide and 28.1 g of 1,4-dibromo-butane were added to the residue obtained in this way. The reaction mix was kept for 24 hours at room temperature land then the solvent was evaporated under reduced pressure. 40 ml of water and 60 ml of methylene chloride were added to the residue obtained in this way and the organic phase was extracted and anhydrified on sodium sulphate and the solvent was evaporated under reduced pressure until a dry residue was obtained. The residue was purified by silica gel chromatography, utilizing an eluent mix constituted by diethyl ether/hexane 1/1 (V/V). The head fractions were collected, the solvent was evaporated under reduced pressure and 8.8 g of 2-(3-benzoilphenyl)propionate of 4-bromobutyl (XXIII) were obtained.

$^1$H-NMR(200 MHz) (CDCl$_3$): 1.53 ppm (d,3H); 1.84 ppm (m,4H); 3.32 ppm (t,2H); 3.78 ppm (q,1H); 4.09 ppm (t,2H); 7.27 (m, 1H, aromatics); 7.38–7.99 (m, 8H aromatics).

Mass spectometry (i.e.): 388 (M$^+$); 309 (M+-Br); 209.

c) 5.5 g of AgNO$_3$ dissolved in 38 ml of acetonitrile were added to 8.8 g of (XXIII) obtained as described under b) dissolved in 35 ml of acetonitrile. The reaction mix was stirred for 24 hours at room temperature and, having added 1.76 g of AgNO$_3$, the reaction mix was stirred for 24 more hours at room temperature and then filtered. The solvent was evaporated from the resulting solution under reduced pressure, obtaining a residue which was treated with methylene chloride.

The mix obtained in this way was filtered again and the organic phase was purified by silica gel pressure chromatography, utilizing an eluent mix constituted by ethyl ether/hexane 3/7 (V/V).

The fractions containing the product were collected, the solvent was evaporated under reduced pressure and 3.4 g of nitric ester of 2-(3-benzoilphenyl)propionate of 4-hydroxybutyl (XVIII) were obtained.

IR (cm$^{-1}$): C=0 1737; ONO$_2$, 1632, 1288; OCO, 1660.

$^1$H-NMR (80 MHz) (CDCl$_3$): 1.48 ppm (d,3H); 1.64 ppm (m,4H); 3.78 ppm (q,1H); 4.08 ppm (m,2H); 4.3 ppm (m,2H); 7.3–7.81 (m, aromatics).

Mass spectrometry (i.e.): 371 (M$^+$); 309 (M$^+$-ONO$_2$); 255.

The anti-inflammatory and anti-platelet aggregation activity as well as the gastrointestinal ulcerogenicity, for instance of nitric esters having the following formulae, were tested by means of biological studies:

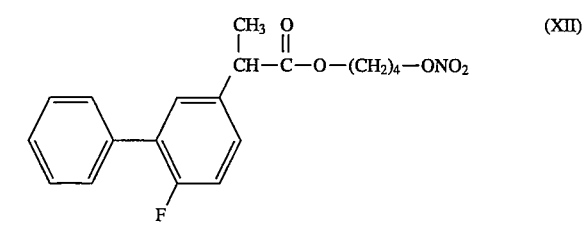
(XII)

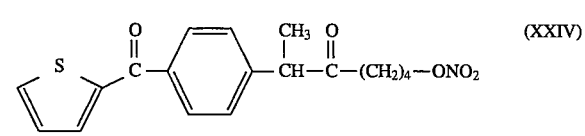
(XXIV)

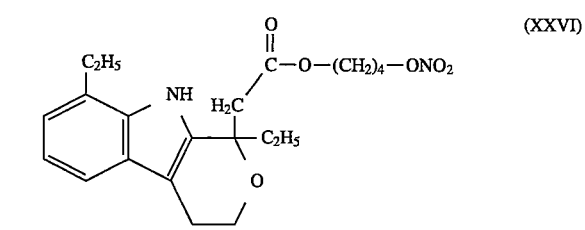
(XXVI)

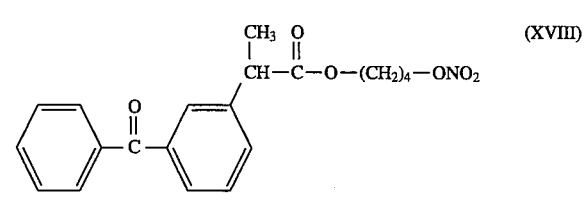
(XVIII)

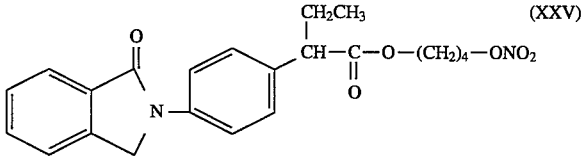
(XXV)

The anti-inflammatory activity of said nitric esters was determined in Wistar rats utilizing the method of the carrageenan paw edema, as reported in C. A. WINTER, E. RISLEY, G. W. NUSS, Proc. Soc. Exp. Biol. Med. 111,544 (1962), while the anti-platelet aggregation activity of said derivatives was determined on human platelets stimulated by arachidonic acid, according to the method described by V. BERTELE et al., Science 220,517 (1983).

The gastrointestinal ulcerability was evaluated by oral administration in the rat.

The anti-inflammatory and anti-platelet aggregation activity as well as the gastrointestinal ulcerability activity of said derivatives are given on Table 1, and are expressed, for each nitric ester indicated, as the power ratio relative to the corresponding acids non functionalized according to the general formula (I), according to this invention. Each value represents the mean of the values obtained by the treatment of 10 animals.

TABLE 1

| COMPOUND STUDIED | ANTI-INFLAM. ACTIVITY | ANTI-AGGREG. ACTIVITY | GASTRO-INTESTINAL ULCER-ABILITY |
|---|---|---|---|
| (XVIII) | 1,25 | 1,35 | 0,20 |
| Ketoprofen | 1 | 1 | 1 |
| (XII) | 1,25 | 1,15 | 0,35 |
| Flurbiprofen | 1 | 1 | 1 |
| (XXIV) | 1,20 | 1,30 | 0,35 |
| Suprofen | 1 | 1 | 1 |
| (XXV) | 1,05 | 1,25 | 0,30 |
| Indobufen | 1 | 1 | 1 |
| (XXVI) | 1,40 | 1,10 | 0,33 |
| Etodolac | 1 | 1 | 1 |

In particular, the derivatives (XVIII) and (XII) submitted to additional studies of a pharmacodynamical nature have given the following results, as shown in the following examples.

RAT CARRAGEENAN PAW EDEMA. Both compounds (XVIII) and (XII) showed an efficacy comparable with the corresponding reference drugs Ketoprofen and Flurbiprofen, the effective doses being in the 1 to 10 mg/kg p.o. range.

RAT ADJUVANT ARTHRITIS. Animals treated for 19 consecutive days (days 3 through 21 after adjuvant injection) with 3 mg/kg p.o. of either compound (XVIII) or (XII) and their corresponding reference compound showed a significant and comparative reduction in the arthritic symptomatology compared to controls.

MOUSE PHENYLQUINONE WRITHING. At doses ranging from 3 to 10 mg/kg p.o., compound (XVIII) and (XII) proved fully effective and their efficaciousness was almost comparable with that of the corresponding reference compounds.

IN VIVO PLATELET AGGREGATION. While both compositions (XVIII) and Flurbiprofen, when administered at the dose of 20 mg/kg p.o. in the rat, inhibited collagen-induced platelet aggregation, the former (66% inhibition versus controls) was significantly more effective than the latter (40%).

BIOCHEMISTRY

PROSTAGLANDIN SYNTHESIS IN THE INFLAMMATORY EXUDATE.

Subcutaneous implantation of carrageenan sponge elicits the infiltration of inflammatory cells, as reported in Nature 284, 271 (1980). Both compounds, (XVIII) and (XII) when administered at the dose of 20 mg/kg p.o. inhibited the formation of prostaglandin E2 in exudate by more than 75% compared with controls and have shown comparative efficacy to the corresponding reference compounds Ketoprofen and Flurbiprofen.

GASTRIC PROSTAGLANDIN SYNTHESIS. Both compounds, (XVIII) and (XII) were studied for prostaglandin synthesis at the same doses (5–20 mg/kg p.o.) utilized for gastric injuries studies. They inhibited significantly and comparatively to the corresponding reference compounds Ketoprofen and Flurbiprofen, the synthesis of prostaglandin E2, the percent of inhibition being more than 90% at the highest dose.

NO RELEASE. Evidence that compounds (XVIII) and (XII) released nitric oxide after their administration was obtained by measurements of plasma nitrate/nitrite levels, as reported in J. Clin. Invest., 85, 264 (1990). One hour after the administration of either (XVIII) or (XII) compound, the plasma nitrate/nitrite levels had significantly increased by more than 50%. Ketoprofen or Flurbiprofen did not affect plasma nitrate/nitrite levels significantly.

Besides, additional biological studies were performed on derivatives (XII) and (XVIII); said studies have provided the following results.

GASTROINTESTINAL TOLERABILITY

RAT GASTRIC MUCOSA INJURY. (XVIII) and (XII) were studied in comparison with the corresponding reference compounds Ketoprofen and Flurbiprofen at doses ranging from 3 to 30 mg/kg p.o., both (XII) and (XVIII) compounds being significantly better tolerated than reference compounds. Ketoprofen or Flurbiprofen caused the onset of gastric damages already at the dose of 3 mg/kg, the severity of such damages being dose-dependent, while (XVIII) or (XII) compounds were well tolerated even at the dose of 30 mg/kg.

The histological evaluation confirmed these findings. Similar differences in the capacity of these compounds to cause gastric and small intestine injury were also observed upon repeated administration of the compounds.

GASTRIC LEUKOCYTE ADHERENCE/VESSEL DIAMETER. An early event in the pathogenesis of NSAID-induced gastric mucosa injury is the adherence of leukocytes to the endothelium of post-capillary venules, as reported in Gastroenterology 103, 146 (1992); Trends Pharmacol. Sci. 13, 129 (1992); Am. J. Physiol. 262, G903 (1992). Using intravital microscopy, the leucokocyte adherence to mesenteric post-capillary venules could be quantified prior to and during a one hour period after the administration of NSAID. Unlike Ketoprofen or Flurbiprofen, (XVIII) or (XII) did not induce significant leukocyte adherence, while increasing the diameter of vessels significantly. No changes in blood pressure were observed.

GENERAL PHARMACOLOGY

A secondary pharmacological evaluation of compound (XVIII) or (XII) was performed in comparison with Ketroprofen or Flurbiprofen. No relevant additional adverse reactions were observed affecting the central nervous, autonomic, cardiovascular, respiratory and gastrointestinal systems.

TOXICOLOGY

ACUTE TOXICOLOGY IN RODENTS.

The acute toxicity of said derivatives (XVIII), (XXIV), (XXV), (XII) and (XXVI) was then evaluated by p.o. administration of a single dose of each compound (XVIII), (XXIV), (XXV), (XII) and (XXVI), utilizing, for each derivative, groups of 10 Swiss mice. Death incidence and the onset of toxic symptoms were reported for a period of 14 days.

Even after administration of a dose of 100 mg/kg of each compound (XVIII), (XXIV), (XXV), (XII) and (XXVI), no apparent toxicity symptoms were noticed in the animals studied.

In particular, preliminary studies on compounds (XVIII) or (XII) were performed in the mouse by two administration routes. No evident toxicity was observed in the animals treated with oral or intraperitoneal doses of 300 mg/kg of either compound.

MAXIMUM TOLERATED DOSE IN NON RODENTS. Preliminary studies indicate that compounds (XVIII) and (XII) were very well tolerated in this animal species that is known to be particularly sensitive to this class of compounds. The animals were administered increasing oral doses up to 30 mg/kg of either compound and no apparent symptoms were observed, while the reference compounds Ketoprofen and Flurbiprofen, administered at the dose of 10 mg/kg caused the death of the animals.

What is claimed is:

1. A nitric ester which has the following general formula:

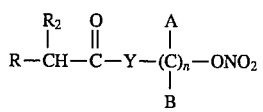  (I)

where:

A and B are hydrogen, linear or branched alkyl chains;

R is:

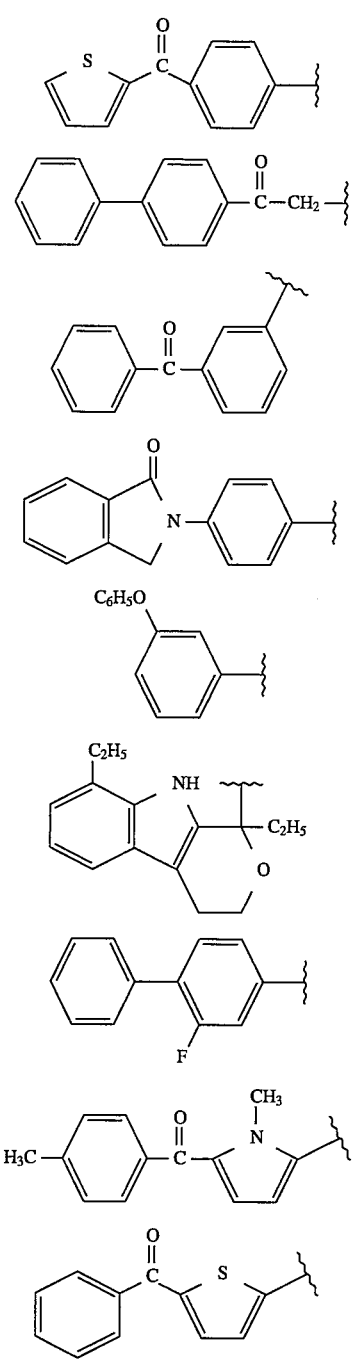

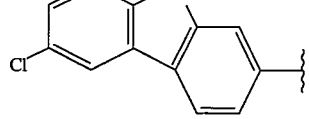  (XXI)

$R_2$ is methyl, ethyl, or a linear or branched alkyl chain of 3 to 12 carbon atoms;

Y is oxygen, NH, or $NR_1$, where $R_1$ is a linear or branched alkyl group; and, n is an integer between 1 and 10.

2. A nitric ester which has the following general formula:

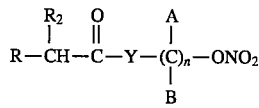  (I)

where:

R is:

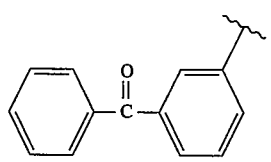  (IV)

$R_2$ is methyl;
A and B are hydrogen;
Y is oxygen; and,
n is four.

3. A nitric ester which has the following general formula:

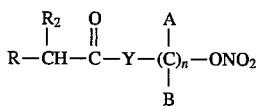  (I)

where:

R is

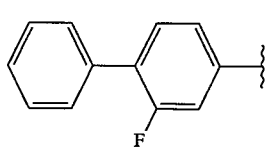  (IX)

$R_2$ is methyl;
Y is oxygen;
A and B are hydrogen; and
n is four.

4. A nitric ester which has the following general formula:

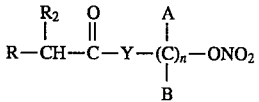  (I)

where:

R is

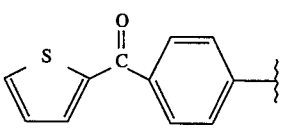  (II)

$R_2$ is methyl;
Y is oxygen;

A and B are hydrogen; and n is four.

5. A nitric ester which has the following general formula:

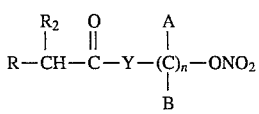 (I)

where:

R is

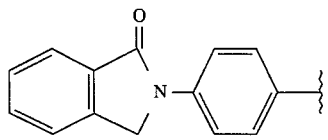 (VI)

$R_2$ is ethyl;

Y is oxygen;

A and B are hydrogen; and n is four.

6. A nitric ester which has the following general formula:

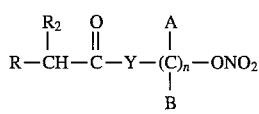 (I)

where:

R is

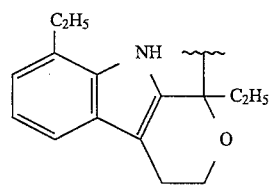 (VIII)

$R_2$ is hydrogen;

Y is oxygen;

A and B are hydrogen; and n is four.

7. A pharmaceutical composition comprising an effective amount of a nitric acid as claimed in any one of claims 1–6.

8. A pharmaceutical composition comprising an anti-inflammatory amount of a nitric acid as claimed in claim 1 and a pharmaceutically acceptable carrier.

9. The pharmaceutical composition of claim 8, wherein said composition is administered in an effective amount to treat rheumatic diseases, immunological disorders, or painful conditions.

10. A pharmaceutical composition comprising a platelet aggregating amount of a nitric acid as claimed in claim 1 and a pharmaceutically acceptable carrier.

11. The pharmaceutical composition of claim 10, wherein said composition is administered in an effective amount to treat diseases affecting the cardiovascular system, myocardia, brain ischemia, or arterial thrombosis.

12. A process for the preparation of a nitric ester according to claim 1 having the following general formula:

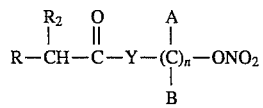 (I)

where:

R is:

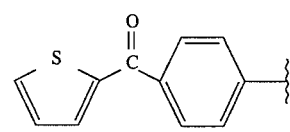 (II)

 (III)

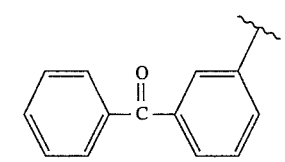 (IV)

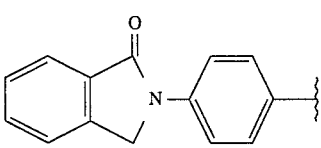 (VI)

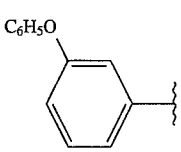 (VII)

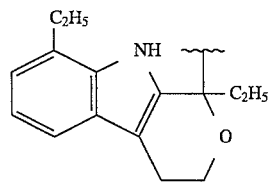 (VIII)

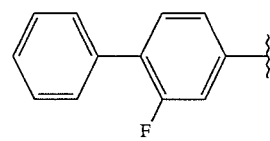 (IX)

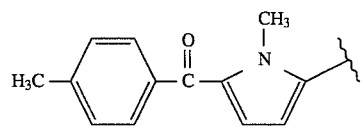 (X)

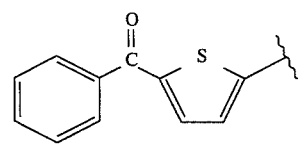 (XXXV)

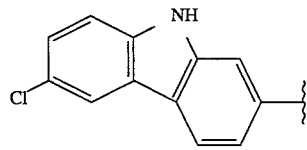 (XXI)

$R_2$ is hydrogen, methyl, ethyl, or a linear or branched alkyl chain of 3 to 12 carbon atoms;

A and B are hydrogen, linear or branched alkyl chains;

Y is oxygen, NH, or $NR_1$;

$R_1$ is a linear or branched alkyl chain, and n is an integer between 1 and 10, comprising the following steps:

a. contacting a sodium salt derivative having the following general formula:

(XIV)

where R is selected from the group consisting of the following structures:

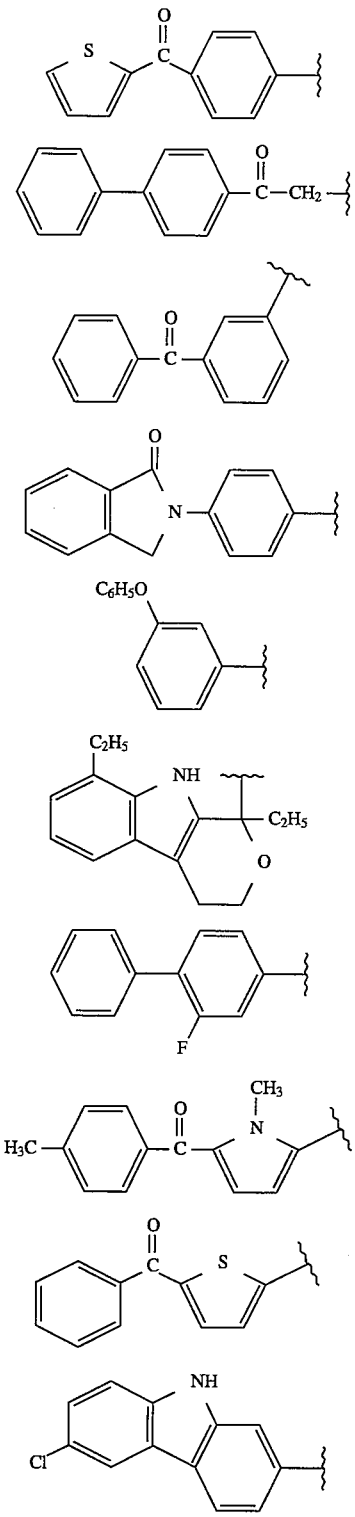

where $R_2$ is hydrogen, methyl, ethyl, or a linear or branched alkyl chain of 3 to 12 carbon atoms; or where derivatives of (XIV) are functionalized to the carboxylic group;
with a compound having the following general formula:

(XV)

where $R_4$ is chlorine, bromine, or $NHR_6$, where $R_6$ is hydrogen, or a linear or branched alkyl chain,
where A and B are hydrogen, linear or branched alkyl chains,
where $R_3$ is chlorine, bromine and iodine, and
where n is an integer between 1 and 10, to obtain monomeric esters or the relative amides; and b. reacting said monomeric esters or said amides with a nitrating agent obtaining nitric esters of derivatives (I).

13. The process of claim 12, wherein said carboxylic group is an acyclic chloride or anhydride.

14. The process of claim 12, wherein said nitrating agent is $AgNO_3$.

15. A process for the preparation of nitric esters according to claim 1 and having the following general formula:

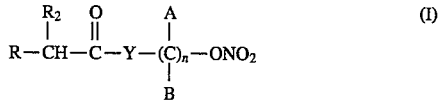
(I)

where A and B are hydrogen or linear or branched alkyl chains;
where $R_2$ is hydrogen, methyl, ethyl, or a linear or branched alkyl chain of 3 to 12 carbon atoms;
where R is:

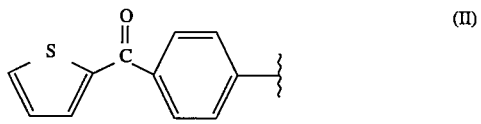
(II)

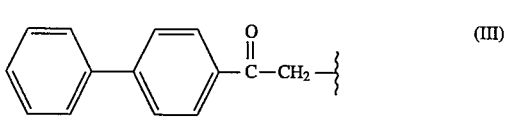
(III)

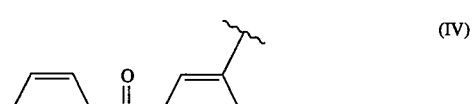
(IV)

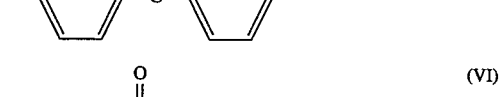
(VI)

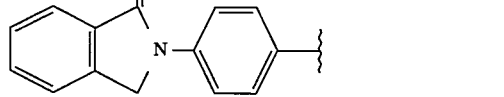

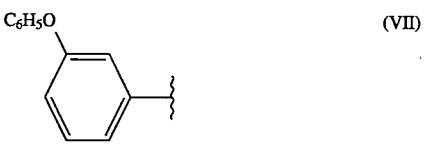
(VII)

-continued

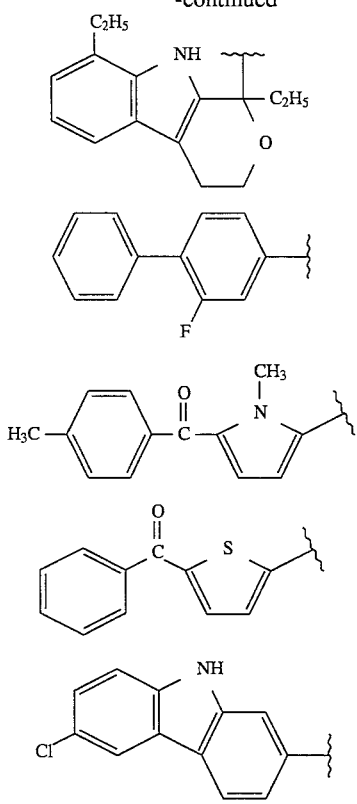

(VIII)

(IX)

(X)

(XXXV)

(XXI)

where Y is oxygen, NH, or NR$_1$;
where R$_1$ is a linear or branched alkyl group; and,
where n is an integer between 1 and 10,
comprising the following steps:
  contacting a sodium salt of derivative having the following general formula:

(XIV)

where R is selected from the group consisting of the following structures:

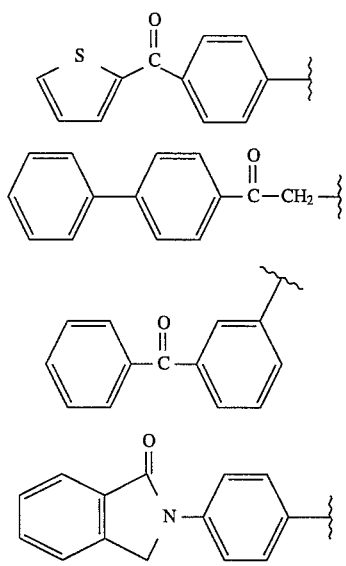

(II)

(III)

(IV)

(VI)

-continued

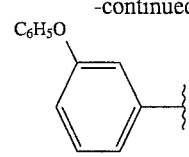

(VII)

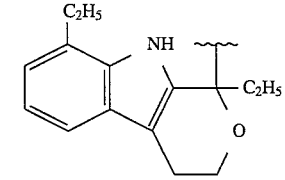

(VIII)

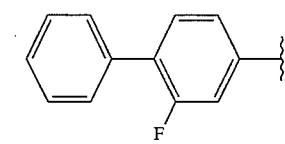

(IX)

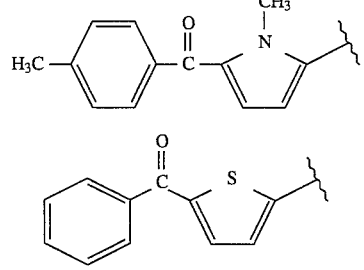

(X)

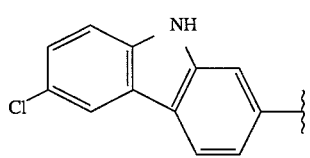

(XXXV)

(XXI)

where R$_2$ is hydrogen, methyl, ethyl, a linear or branched alkyl chain of 3 to 12 carbon atoms; or
where derivatives of (XIV) are functionalized to the carboxylic group;
with a compound having the following general formula:

(XVI)

where R$_4$ is chlorine, bromine, or NHR$_6$, where R$_6$ is hydrogen, or a linear or branched alkyl chain,
where A and B are hydrogen, linear or branched alkyl chains, and
where n is an integer between 1 and 10,
to obtain monomeric esters or the relative amides; and,
b. reacting said monomeric esters or said amides with a halogenating compound to obtain said monomeric esters or said amides, which are characterized by the presence of a terminal halogen group; and,
c. reacting said monomeric esters or said amides of step b with a nitrating agent to obtain the nitric esters of derivatives (I).

16. The process of claim 15, wherein said carboxylic group is an acyclic chloride or anhydride.

17. The process of claim 15, wherein said nitrating agent is AgNO$_3$.

* * * * *